United States Patent [19]
Jones et al.

[11] Patent Number: 5,844,198
[45] Date of Patent: Dec. 1, 1998

[54] TECHNIQUE FOR LASER WELDING DISSIMILAR METALS

[75] Inventors: Stephen M. Jones, Canyon Country; Arthur A. Campbell, Stevenson Ranch; Jeffrey L. Pennala, Long Beach, all of Calif.

[73] Assignee: Pacesetter, Inc., Sylmar, Calif.

[21] Appl. No.: 686,997

[22] Filed: Jul. 24, 1996

Related U.S. Application Data

[62] Division of Ser. No. 550,907, Oct. 31, 1995, Pat. No. 5,571,140.

[51] Int. Cl.$^6$ ................................................ B23K 26/00
[52] U.S. Cl. ......................................................... 219/121.64
[58] Field of Search ........................ 219/121.63, 121.64, 219/118, 56.1, 56.22, 56.21, 56; 228/4.5, 6.2, 233.2, 262.44; 607/119

[56] References Cited

U.S. PATENT DOCUMENTS

| 5,067,903 | 11/1991 | Szyszkowski | 439/55 |
|---|---|---|---|
| 5,235,742 | 8/1993 | Szyszkowski | 29/856 |
| 5,282,841 | 2/1994 | Szyszkowski | 607/36 |
| 5,306,891 | 4/1994 | Fleming et al. | 219/121.64 |
| 5,343,014 | 8/1994 | Ogino et al. | 218/121.64 |
| 5,522,872 | 6/1996 | Hoff | 607/119 |

FOREIGN PATENT DOCUMENTS

| 55-46457 | 4/1980 | Japan | 219/56.1 |
|---|---|---|---|
| 57-160590 | 10/1982 | Japan | . |
| 58-58988 | 4/1983 | Japan | 219/121.64 |
| 58-107291 | 6/1983 | Japan | 219/121.64 |
| 3-230882 | 10/1991 | Japan | 219/121.64 |

*Primary Examiner*—Geoffrey S. Evans

[57] ABSTRACT

For an implantable medical devices, a system is provided for welding electrically conductive ribbon, typically stainless steel, to electrically conductive wire, typically platinum, the melting point of steel being substantially lower than that of platinum. An aperture is formed in the ribbon having an opening smaller than that of the wire. The ribbon is engaged with the wire such that the aperture is generally coextensive with the wire. Thereupon, a pulse laser beam is directed transversely of the ribbon through the aperture and onto the wire to simultaneously melt the wire and the ribbon and to create a homogeneous mix of the molten steel and platinum in the region surrounding the aperture. Thereafter, operation of the laser beam is discontinued to allow solidification and thereby achieve a welded connection between the ribbon and the wire.

8 Claims, 4 Drawing Sheets

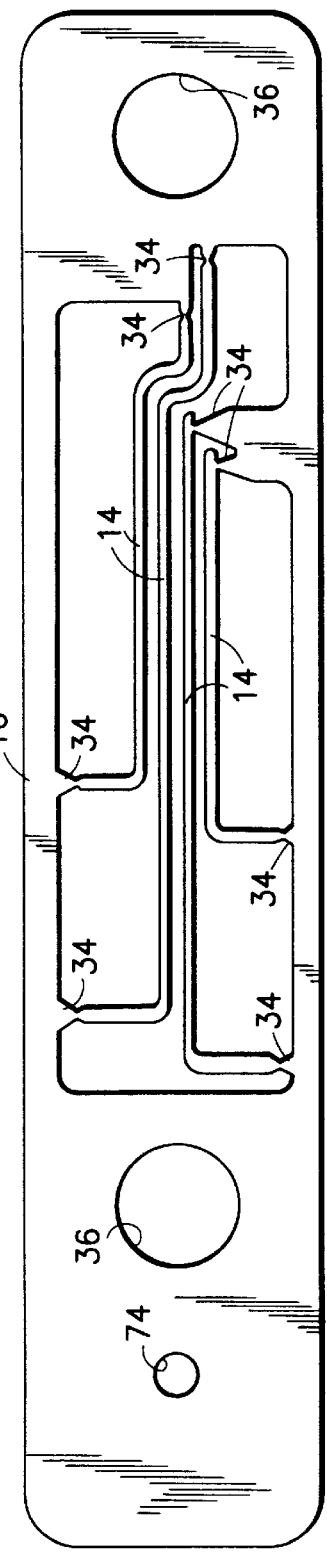
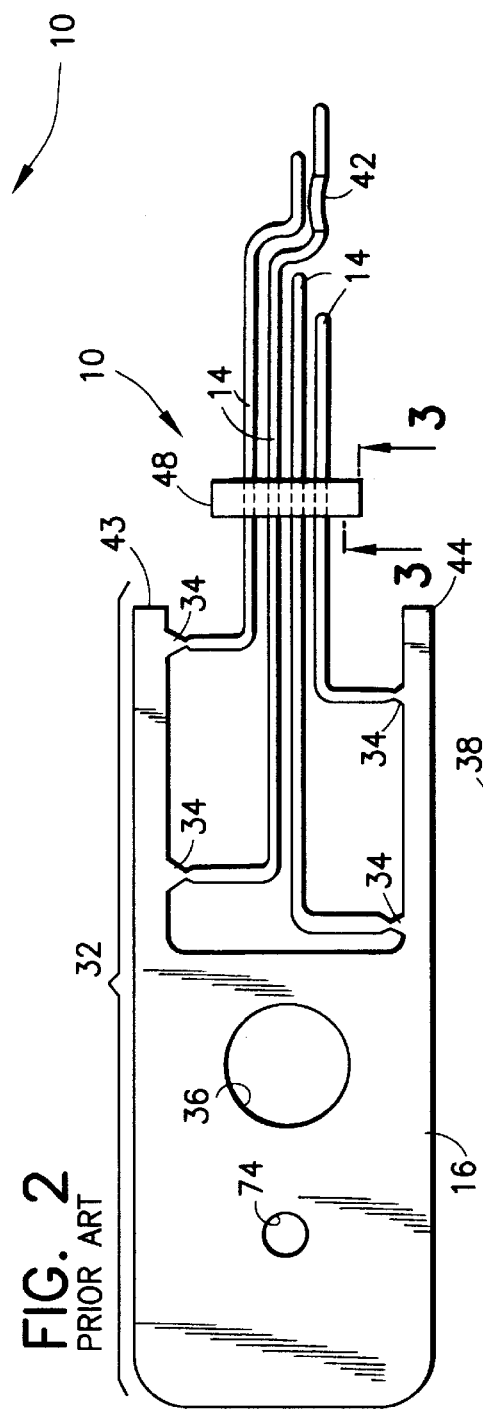
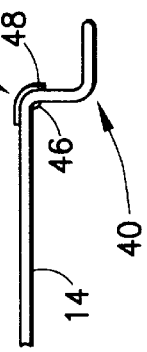
FIG. 1 PRIOR ART
FIG. 2 PRIOR ART
FIG. 3 PRIOR ART

TECHNIQUE FOR LASER WELDING DISSIMILAR METALS

This is a divisional of application(s) Ser. No. 08/550,907 filed on Oct. 31, 1995, now U.S. Pat. No. 5,571,146.

FIELD OF THE INVENTION

This invention relates generally to improvements in a technique for welding dissimilar metals. More particularly, this invention relates to a novel technique for conductively interconnecting electrical components in an implantable medical device, or the like. The invention is particularly designed to facilitate electrical interconnection of pacemaker lead connector blocks with feedthrough terminals of an implantable heart pacemaker unit or similar device.

BACKGROUND OF THE INVENTION

Implantable medical devices of the type having electrical circuit components are well known in the medical arts. In one particularly common form, the implantable device comprises a pacemaker unit having an appropriate electrical power supply and related control circuitry for use in electrically stimulating a patient muscle, such as the heart. Such pacemaker units commonly include a hermetically sealed case, or housing, within which the power supply and control circuitry are protectively encased, in combination with one or more conductive pacemaker leads extending from the housing to the selected muscle structure within the patient. Feedthrough terminals on the pacemaker housing accommodate hermetically sealed passage of electrical conductors to the housing exterior for appropriate connection to the pacemaker lead or leads, typically through the use of so-called connector blocks having setscrews, or the like, for secure lead attachment. Not all connector blocks utilize setscrews. Some leads are held in place by other mechanical means, such as compression seals. The connector blocks and associated feedthrough conductors disposed externally of the pacemaker housing are commonly encased within a hermetically sealed head structure, such as an insulative head of cast epoxy, or the like.

In the past, considerable research and development activity has focused upon the design of feedthrough terminals for permitting pacing signals to be transmitted from the hermetically sealed unit housing. Similarly, significant efforts have been directed toward the design of pacemaker lead connector blocks for obtaining a secure, yet hermetically sealed, electromechanical connection to pacemaker leads. However, comparatively little attention has been directed to the design of conductors and related installation methods for electromechanically interconnecting the feedthrough terminals with the associated lead connector blocks. To the contrary, available pacemaker units have predominantly utilized elongated wires extending from the feedthrough terminals and individually shaped by bending for appropriate connection by welding, or the like, to the associated connector blocks. Unfortunately, the close working space provided in a desirably compact implantable device makes this wire bending and shaping procedure both tedious and time-consuming. Moreover, in pacemaker units having multiple feedthrough terminal conductors, significant attention and skill are required to maintain the conductor wires in sufficiently spaced array to avoid short circuit failures during pacemaker unit operation.

Until recently, there existed a significant need for improvements in devices and methods for electrically interconnecting feedthrough terminals with lead connector blocks in a heart pacemaker unit or other implantable medical device, particularly with respect to permitting the desired electrical interconnections to be made quickly and easily with multiple conductors arranged and maintained in spaced relation to prevent short circuit failures. However, this need was fulfilled by the commonly-assigned U.S. Pat. Nos. 5,282,841; 5,235,742; and 5,067,903; to Szyszkowski, the disclosures of which are fully incorporated herein by reference. As disclosed in those patents, a ribbon conductor set is provided for facilitated electrical connection of feedthrough terminals and lead connector blocks in an implantable medical device, such as a heart pacemaker unit, or the like. The ribbon conductor set comprises a plurality of conductor ribbons formed as a set in predetermined number, spacing, and geometry to extend between multiple conductors at one or more feedthrough terminals and a plurality of lead connector blocks individually associated with the feedthrough conductors. The conductor ribbons are adapted for installation as a group into a pacemaker unit, and in an orientation which accommodates relatively simple connection to the feedthrough terminals and connector blocks by spot welding, or the like.

SUMMARY OF THE INVENTION

The commonly used form of welding which is satisfactory for this purpose has been resistance welding which unfortunately is operator dependent with many variances—electrode wear, force and voltage, operator handling, etc. Note: resistance welders are less expensive than laser welders. The inventor came to recognize that laser welding the 316L stainless steel ribbon (typically dimensioned 0.006" of an inch thick and 0.020 inches wide) to the stainless steel connector block and platinum feedthrough wire (typically having a 0.012 inches diameter) would be a preferable alternative method to resistance welding. However, the problem was complicated by the fact that the stainless steel ribbon and the platinum feedthrough wire have different melt temperatures (1,398° C. and 1,773° C., respectively).

With the existing ribbon configuration, the laser welding of these two different components would be impossible. The idea was to melt the platinum feedthrough wire and stainless steel ribbon simultaneously. In order to achieve a good melt and to avoid creating voids in the platinum melt due to outgassing, two things were initially determined to be necessary. The first was to have intimate contact between the two materials. The second was to change the configuration of the ribbon design to allow a simultaneous melt of the two materials. This simultaneous melt would only be possible if the ribbon had a hole in it to allow the focal point of the laser beam to pass through and melt the platinum first. While the beam energy is being absorbed by the platinum wire, the surrounding stainless steel ribbon edges would melt creating a mix of stainless steel and platinum at the contact points around the hole in the ribbon. The energy density of the laser beam is highest at the focal point; therefore, the platinum would melt first. Furthermore, the outside edge of the laser beam has a lower energy density. The hole in the ribbon must be at a diameter that allows the focal point of the laser beam to pass while small enough to allow the outside edge of the beam to melt the stainless steel ribbon. The ribbon must also have enough surrounding material around the hole so it does not melt or lose shape during the weld process. The inside hole dimension was determined to be approximately 0.010 inches ±0.002 with an outside dimension of approximately 0.040 inches ±0.002. This is ideal for a 0.012 inches diameter platinum wire. The wire is laid underneath the hole to completely cover the hole. The 0.010 inches inside hole is large enough to allow the laser beam to pass through, yet small enough to allow the melt of the inside edges of the ribbon hole and wire simultaneously. The outside dimension (0.040 inches) is large enough to dissipate the heat around the heat affected zone. As the effort proceeded, it came to be recognized that a third necessary ingredient of the invention involved the laser parameters, specifically, providing a pulse laser operated with specially shaped pulses.

This particular design is relevant to many products that involve dissimilar metals. In short, the key to this technique is the hole dimension and the laser parameters.

Accordingly, a primary object of the present invention is to provide a technique for welding dissimilar metals having different melt temperatures. Another object of the invention is to provide a novel technique for welding stainless steel ribbon and platinum wire while avoiding cracking and voids in the weld joint.

A further object of the invention is to provide a novel technique for conductively interconnecting electrical components in an implantable medical device, or the like.

Still another object of the invention is to provide a novel technique for welding stainless steel ribbon and platinum wire by forming an aperture in the ribbon with an opening smaller than the diameter of the wire, positioning the ribbon in engagement with the wire such that the aperture in the ribbon is generally coextensive with the wire, directing a laser beam transversely of the ribbon through the aperture in the ribbon and onto the wire to simultaneously melt the wire and the ribbon in the region of the aperture and create a homogenous mix of the first material with the second material in the region surrounding the aperture.

Yet a further object of the invention is to perform such a technique by operating a pulse laser with specially shaped pulses.

Other and further features and advantages of the present invention will become more apparent from the following detailed description, taken in conjunction with the accompanying drawings which illustrate, by way of example, the principles of the invention. Throughout the specification, like numerals refer to like parts.

BRIEF DESCRIPTION OF THE DRAWINGS

The accompanying drawings illustrate the invention. In such drawings wherein like numerals refer to like parts:

FIG. 1 is a plan view illustrating a known ribbon conductor set supported within an integrally formed frame;

FIG. 2 is a plan view of the ribbon conductor set similar to FIG. 1, but illustrating the ribbon conductor set subsequent to die cutting and shaping, and removal of a portion of the support frame;

FIG. 3 is a fragmented elevational view taken generally on the line 3—3 of FIG. 2;

DETAILED DESCRIPTION OF THE PREFERRED EMBODIMENT

Figure 4:
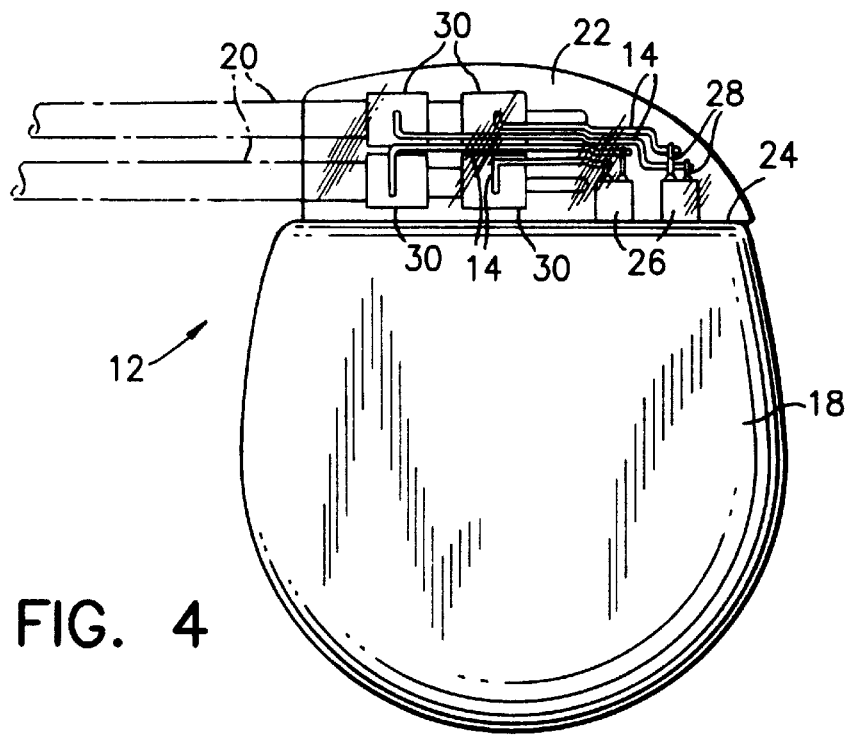
FIG. 4 is a front elevational view of a resultant finished pacemaker unit embodying the present invention having the feedthrough terminals, the ribbon conductor set, and the connector blocks encapsulated within a cast head of a suitable insulative epoxy.

Turn now to the exemplary drawings, and initially to FIGS. 1–3, wherein a ribbon conductor set is referred to generally by the reference numeral 10. The ribbon conductor set is provided for quickly and easily interconnecting electrical components in an implantable medical device, such as a heart pacemaker unit 12, or the like, as viewed in FIG. 4. The ribbon conductor set 10 provides a plurality of conductor ribbons 14 in a predetermined shape and spatial array in accordance with the geometry of the electrical components to be interconnected. This shaped array of conductor ribbons 14 is supported as a unit or group by an integral support frame 16 for facilitated handling and placement in the course of connection to the associated electrical components.

The ribbon conductor set 10 of the present invention is designed particularly for use in an implantable medical device such as a heart pacemaker unit 12 (FIG. 4). In this regard, heart pacemaker units are generally known in the art for use in electrical stimulation of the heart muscle to regulate patient heartbeat in a controlled manner. The pacemaker unit 12 normally includes an appropriate power source and related electronic circuitry encased within a compact, hermetically sealed, housing or case 18 adapted for implantation directly into the body of a patient at a selected convenient location. The unit produces a timed sequence of pacing pulses which are coupled to one or more conductive pacemaker leads 20, with the illustrative drawings depicting the pacemaker unit 12 to include a pair of pacemaker leads 20 for so-called duplex mode operation. The pacemaker leads 20 extend from the unit housing 18 for implantation of their distal ends (not shown) into target muscle tissue to be stimulated.

As shown best in FIG. 4, the pacemaker unit 12 includes a head 22 on the unit housing 18, wherein the head 22 includes means for electromechanically anchoring the pacemaker leads 20 in conductive relation with the pacing signals generated by the circuitry components within the housing 18. More specifically, the pacemaker housing 18 defines a relatively flat mounting platform 24 at one edge thereof. One or more so-called feedthrough terminals 26 project upwardly from this platform and provide hermetically sealed structures of a type known in the art for passing electrical conductors from the interior of the housing 18. The illustrative drawings show a pair of feedthrough terminals 26 each including a pair of short upstanding terminal conductors 28, thereby providing a total of four conductors 28 for use in duplex mode pacemaker unit operation. These feedthrough terminal conductors 28 are respectively connected by means of the ribbon conductor set 10 of the present invention to a corresponding set of four connector blocks 30 adapted for electromechanical connection to the pacemaker leads 20. Subsequent to electrical interconnection of the feedthrough terminal conductors 28 with the connector blocks 30, as will be described in more detail, these components are encapsulated within a block of insulative epoxy material, or the like, which is cast in place to define the head 22 maintaining the various components in the desired hermetically sealed and predetermined interspatial relation.

The apparatus and method of the present invention is designed to facilitate the process of interconnecting the feedthrough terminal conductors 28 with the connector blocks 30. More particularly, the ribbon conductor set 10 provides a preshaped and prespaced array of conductive elements which can be handled as a unitary set or group for rapid yet accurate placement and appropriate connection by resistance spot welding, or the like. The ribbon set 10 is adapted for cost-efficient manufacture by die cutting and/or stamping processes to yield detailed yet reproducible ribbon shapes in conformance with the geometry of the feedthrough terminals and connector blocks to be interconnected. Importantly, when the ribbon set is mounted in place, the individual conductor ribbons 14 are maintained in sufficient spacing to substantially eliminate risk of short circuit failures.

With reference to FIG. 1, the ribbon conductor set 10 is formed from sheet stock of a suitable conductive material to include the set of conductor ribbons 14 carried within the surrounding support frame 16. As shown in the initial stages of formation, the support frame 16 is generally coplanar with the conductor ribbons 14, with each ribbon 14 having an individualized elongated shape supported at its opposite ends by a pair of narrow frets 34 on the support frame 16. In a preferred method of formation, this frame and ribbon set combination is formed by etching thin sheet stock of stainless steel or platinum alloy, or the like, to produce the desired ribbon pattern, wherein this etched sheet stock may have a thickness on the order of a few thousandths of an inch. Alternately, etching, cutting and/or stamping processes may be used. Desirably, the support frame 16 includes one or more large ports 36 formed therein to permit accurate placement into process tools and fixtures.

FIGS. 2 and 3 illustrate the ribbon conductor set 10 subsequent to an etching, stamping and/or cutting process step for shaping the individual conductor ribbons 14 to an appropriate three-dimensional geometry. More specifically, the ribbon set can be seated into an appropriate die tool for shaping each ribbon 14 to include one or more bends deviating from the plane of the support frame 16. FIG. 3 illustrates all four ribbons 14 to include a common rearward bend 38 in close association with a return bend 40. In addition, FIG. 2 shows one of the ribbons 14 to include a generally semicircular bend 42 for clearance with a feedthrough terminal 26, as will become more apparent. During this die stamping step, a portion of the support frame 16 is desirably removed by trimming the frame at points 43 and 44, and by severing the frets 34 at one common end of the conductor ribbons 14. As a result, the conductor ribbons 14 project generally in somewhat cantilevered relation from the remaining portion of the support frame 32 which remains connected to the ribbons by means of the remaining frets 34.

The conductor ribbons 14 are desirably provided with additional support means to maintain the interribbon spacing and to minimize risk of ribbon damage during subsequent handling. For example, as shown in FIG. 3, an elongated bead 46 of epoxy, or the like, may be placed and cured along the conductor ribbons 14 such as at the inboard side of the bend 38 to support the ribbons with respect to each other. Alternatively, or in addition, a strip of tape 48 such as insulating tape of Kapton film, or the like, may be used as a temporary support for the fragile ribbons 14.

Figure 5:
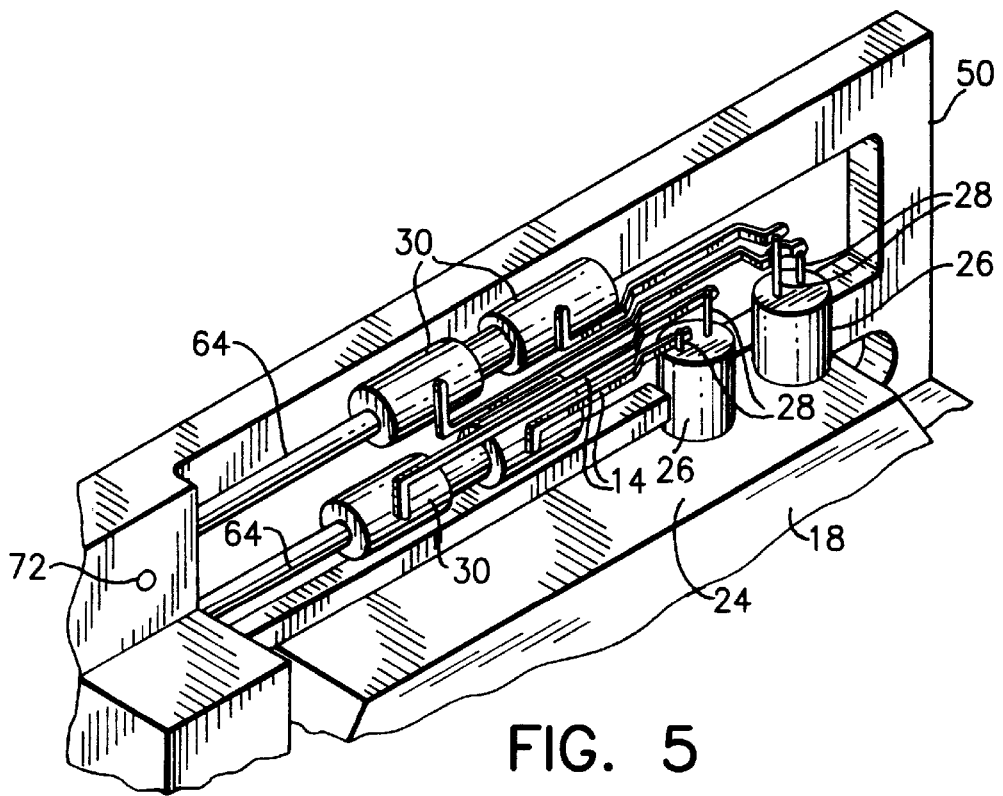
FIG. 5 is an enlarged fragmented perspective view showing the ribbon conductor set electrically interconnecting the lead connector blocks with feedthrough terminal conductors, and with the support frame for the ribbon set being removed.

A fixture 50 (FIG. 5) may be of the type disclosed in the aforementioned Szyszkowki patents for use in supporting the various components in a convenient arrangement during placement and mounting of the ribbon conductor set 10. Such a fixture may also be used to position the feedthrough terminals 26 and their respective short protruding conductors 28 at predetermined locations relative to the feedthrough terminals 26. Additional anchoring of the pairs of connector blocks 30 may be provided by temporary insertion of lead pins 6.4 into the connector blocks.

With the pacemaker unit housing 18 and the connector blocks 30 in place, the ribbon conductor set 10 is easily placed in overlying relation over the pacemaker components. A short locator pin 72 on the fixture 50 is adapted for reception into a mating aperture 74 in the support frame 16 to predetermine the position of the ribbon set. In this position, the free ends of the individual conductor ribbons 14 align easily and accurately with the respective feedthrough terminal conductors 28, and the opposite fret-supported ends of the ribbons 14 align with the respective connector blocks 30. In this orientation, both ends of each ribbon 14 can be attached quickly and easily to the associated components. A known method of attachment is resistance spot welding but a preferred method, as will be described below, is laser pulse welding. Thereupon, the remainder portion of the support frame 16 can be removed quickly and easily by severing at the frets 34. The strip of support tape 48, if used, may be removed at a convenient time typically subsequent to ribbon attachment to the underlying components.

The resultant head subassembly, including the connector blocks 30 interconnected via the conductor ribbons 14 with the feedthrough conductors 28, provides an accurate and highly attractive electrical interconnection. The pacemaker unit 12 including this head subassembly is removed from the fixture 50 and appropriately processed to cast the epoxy head 22. This head 22, as viewed in FIG. 4, encapsulates the electrical components with an insulative and hermetic seal material. This epoxy head further supports the components in the desired predetermined spatial relation, and in a manner which is fully compatible with the epoxy bead 46 (FIG. 3) used to support the ribbons 14 during processing.

As noted above, this invention relates to the ability to laser weld two dissimilar materials, typically, but not intended to be limiting of the invention, 0.012 inches diameter platinum wire and 0.006 inches thick by 0.020 inches wide 316L stainless steel conductor ribbon, using a technique referred to as pulse shaping. The welding of 0.012 inches diameter platinum and platinum-iridium (90/10 respectively) feedthrough wire to 0.006 inches thick by 0.020 inches wide 316L stainless steel conductor ribbon has been performed by resistance welding methods. This process of attaching two dissimilar materials is very common in the medical industry as well as throughout other industries. However, to melt two dissimilar metals such as platinum or platinum-iridium wire to stainless steel conductor ribbon using lasers, for example, by using a neodymium yttrium-aluminum-garnet (Nd:YAG) laser with a single pulse has been attempted without success. One of many problems in fusing platinum or platinum-iridium wire to stainless steel is the differences in melt temperatures of those materials. Platinum has a melt temperature of 1,773.5° C. Stainless steel 316L has a melt temperature of 1,398° C. Another problem was the configuration of the two materials involved. One is flat and the other is round. Therefore, the point of contact between the two materials is a tangential point. This problem becomes very difficult because in order to melt the stainless steel the temperature must be at least 1,398° C. This is obviously insufficient eat to melt the platinum. However, melting the platinum at 1,773.5° C. would vaporize the stainless steel due to the amount of heat introduced into a small part of only 0.006 inches thick and 0.020 inches wide.

Figure 6:
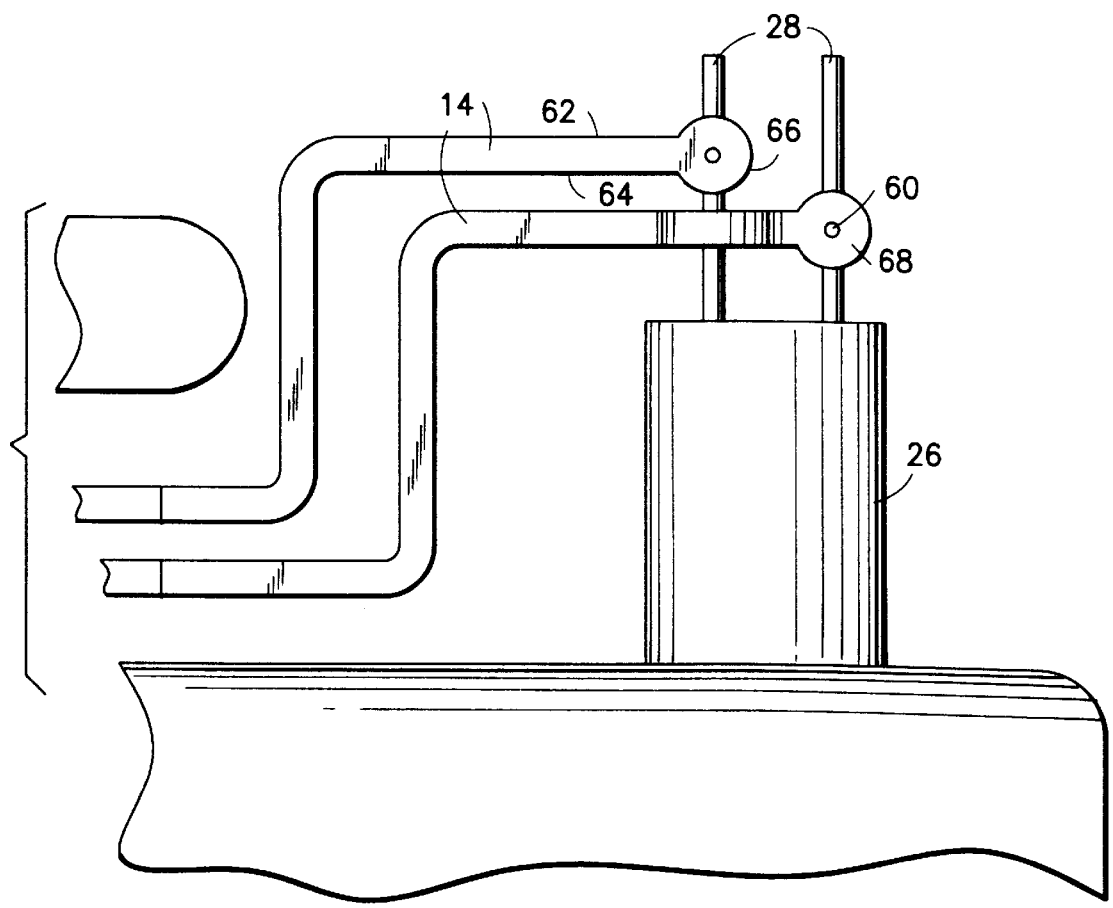
FIG. 6 is an enlarged front elevational view of parts depicted in FIG. 4, illustrating a portion of the ribbon conductor set, modified according to the invention, overlying the short protruding terminal conductors and affixed thereto by the pulse laser welding technique of the invention.
Figure 7:
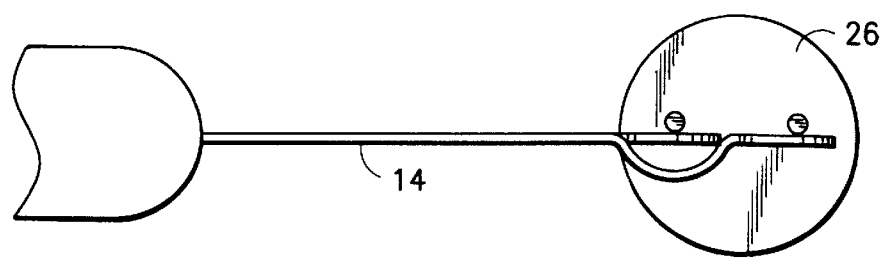
FIG. 7 is a detail plan view of the components illustrated in FIG. 6.

Therefore, a design modification, part of the invention, was made to the conductor ribbon to allow simultaneous melt of the two materials. Viewing FIGS. 6 and 7, this modification includes providing an aperture 60 in the ribbon portion that lies over the wire. The stainless steel ribbon 14 has opposed first and second edges 62, 64, respectively, and a terminal edge 66 joining the first and second edges and is approximately 0.020 inches wide by approximately 0.006 inches thick. Typically, but not being limiting of the invention, the aperture in the stainless steel ribbon has a diameter of approximately 0.008 inches, the platinum wire has a diameter of approximately 0.012 inches, and a terminal end 68 of the ribbon has an outside diameter of approximately 0.020 inches. However, this design was only part of the solution. The single laser pulse was ineffective in creating a homogenous melt of the two materials. Furthermore, the problem of cracked welds and voids in the weld joint was still evident.

The initial attempts at welding the two materials, using a single pulse neodymium yttrium-aluminum-garnet laser (ND:YAG) 1.06 micrometer wavelength laser beam, showed cracking in the stainless steel as well as void areas in the weld joint. This was due to the single pulse shape most commonly used in laser processing. This simple pulse shape has a time (pulse width) and a sector height. The area under a graphed rectangle (not illustrated) which would depict this operation represents the energy that will be delivered. It will be recognized, however, that such a simple pulse shape would not have a smooth profile for controlling the amount of energy that would be put into the parts. Smooth profile allows pre-pulses to melt the materials while controlling the weld pulse to lessen cracking in the weld area.

The JK700 series of lasers manufactured by JK Lumonics, Inc. of Rugby, England offer a way of controlling the amount of energy by allowing the setting of different pulse widths and heights within a pulse. Turn now to FIG. 8 which is a graph illustrating the operation of a pulse laser according to the invention. This particular model of laser provides a maximum of 20 sectors per pulse shape. The minimum pulse width is 0.5 milliseconds (ms) for the main sector. Main sector is the standard rectangular pulse that is typical of lasers without pulse shaping. All other sectors have a minimum of 0.3 ms. The maximum total pulse width is 20 ms. The overall effect is a profile which looks like a histogram and the laser output, using the technique of the invention, then results in a smoother more controllable profile. This is beneficial in minimizing problems in materials that are prone to cracking.

Figure 8:
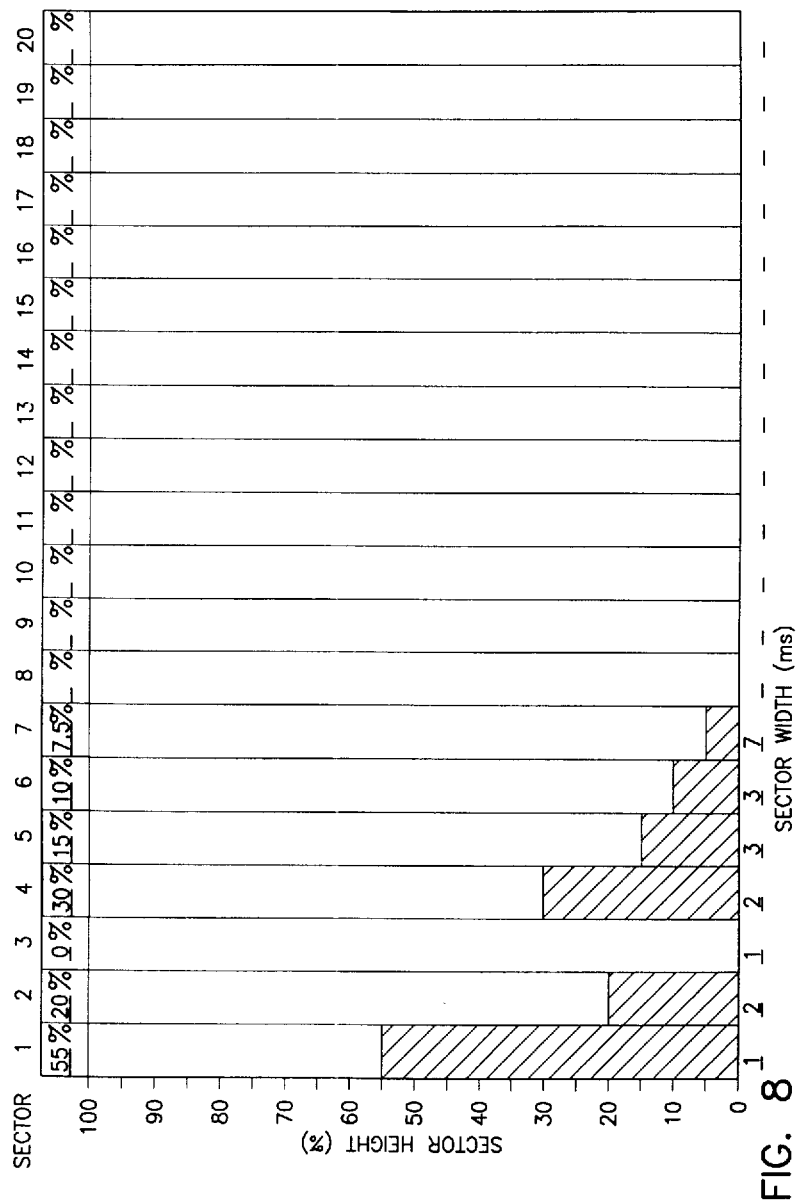
FIG. 8 is graph depicting the operation of the pulse laser according to the invention.

With this new tool, the ability to melt two very dissimilar metals became possible. Using a JK702 250 watt solid state laser, a pulse shape was developed to weld the platinum wire to the stainless steel ribbon. As illustrated in FIG. 8, the pulse shape is comprised of seven sectors. Each sector has a unique pulse width and pulse height. The pulse shape can be the to begin with a pre-pulse of two sectors. In the following recitation, all values are only approximations. The first sector is 1 millisecond (ms) long with a pulse height of 55%, that is, 55% of the maximum pulse height of which the chosen laser is capable. During this portion of the pulse, the platinum is actually melted and the molecular structure altered so that the laser beam is no longer reflected but is, in fact, absorbed by the wire. The second sector, which causes melting of the stainless steel is 2 ms long and has a pulse height of 20%. The third sector is 1 ms long with a pulse height of 0%. This third sector is intended to be the cool-down time between the pre-pulse and weld pulse. It allows the wire to flatten out against the ribbon to result in a larger contact surface between the ribbon and the wire. The fourth sector has a pulse width of 2 ms and a pulse height of 30%. The fifth sector has a pulse width of 3 ms and a pulse height of 15%. The sixth sector has a pulse width of 3 ms and a height of 10%. The seventh and final sector has a pulse width of 7 ms and a height of 7.5%. The fourth through the seventh sectors enable the heat to the connection to taper off in a controlled manner while retaining the engaged parts in a liquified state. Cracking is thereby avoided.

The seven sectors have a combined pulse width of 19 milliseconds. The frequency was set to 10 Hertz (Hz), although any frequency within the range of 5 Hz and 100 Hz could be used, as is typically available to a pulse laser of the type used for the present invention. The total energy delivered to the components is 2.00±0.05 joules. The average power is between 19.5 watts and 20.5 watts. The peak power is approximately 110 watts. Some other operating parameters are important for operation of the invention. As to pulse height, sector 1 may not be less than sector 2, sector 4 must be less than sector 1, and the last four sectors must be successively decreasing. The time range for the total of all the sectors is between approximately 16 and 20 ms and the sum, timewise, of sectors 4–7 must be greater than that of sectors 1–3. Preferred parameters, sector by sector, may be related as approximations as follows:

1. the first sector having a width in the range of approximately 0.5 to 1.5 milliseconds and a height in the range of approximately 50% to 60%;
2. the second sector having a width in the range of approximately 1.5 to 2.5 milliseconds and a height in the range of approximately 15% to 25%;
3. the third sector having a width in the range of approximately 0.5 to 1.5 milliseconds and having no height;
4. the fourth sector having a width in the range of approximately 1.5 to 2.5 milliseconds and a height in the range of approximately 25% to 35%;
5. the fifth sector having a width in the range of approximately 2.5 to 3.5 milliseconds and a height in the range of approximately 10% to 20%;
6. the sixth sector having a width in the range of approximately 2.5 to 3.5 milliseconds and a height in the range of approximately 5% to 15%; and
7. the seventh sector having a width in the range of approximately 6.5 to 7.5 milliseconds and a height in the range of approximately 0% to 10%.

The pulse shape and energy combination as just described, has made it possible to laser weld two very different materials and has opened a door to fusion technology that only a short time ago seemed impossible. Specifically, the pulse shape and energy related above proved to be an optimum configuration for melting the platinum wire and stainless steel materials together and the cracking and voids that had been observed with the single pulse shape were not present with this new technique.

While preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. A method of welding electrically conductive ribbon comprising a first material having a first melting point to electrically conductive wire comprising a second material having a second melting point, the first melting point being substantially lower than the second melting point, the method comprising the steps of:

(a) forming an aperture in the ribbon with an opening smaller than the diameter of the wire;

(b) positioning the ribbon in engagement with the wire such that the aperture in the ribbon is generally coextensive with the wire;

(c) directing a laser beam transversely of the ribbon through the aperture in the ribbon and onto the wire to simultaneously melt the wire and the ribbon in the region of the aperture and create a homogeneous mix of the first material with the second material in the region surrounding the aperture; and (d) discontinuing operation of the laser beam to allow solidification of the homogeneous mix of the first material with the second material in the region surrounding the aperture to thereby achieve a welded connection between the ribbon and the wire.

2. A method, as set forth in claim 1:

wherein the first material is stainless steel; and wherein the second material is platinum, or platinum iridium.

3. A method, as set forth in claim 2:

wherein the stainless steel ribbon has opposed first and second edges and a terminal edge joining the first and second edges and is approximately 0.020 inches wide by approximately 0.006 inches thick;

wherein the aperture in the stainless steel ribbon has a diameter of approximately 0.008 inches; and wherein the platinum wire has a diameter of approximately 0.012 inches.

4. A method, as set forth in claim 1, wherein step (c) is performed by a pulse laser.

5. A method, as set forth in claim 1, wherein step (c) is performed by a solid state pulse laser.

6. A method, as set forth in claim 5, wherein the total energy delivered to the ribbon and to the wire during step (c) is approximately 2.00+/−0.05 joules at an average power between approximately 19.5 and 20.5 watts with peak power being approximately 110 watts.

7. A method, as set forth in claim 1:

wherein step (c) is performed by a pulse laser;

wherein the pulse width is in the range of approximately 16 to 20 milliseconds; and wherein the pulse shape generated by the pulse laser comprises seven successive sectors including:

a first sector having a width in the range of approximately 0.5 to 1.5 milliseconds and a height in the range of approximately 50% to 60%;

a second sector having a width in the range of approximately 1.5 to 2.5 milliseconds and a height in the range of approximately 15% to 25%;

a third sector having a width in the range of approximately 0.5 to 1.5 milliseconds and having no height;

a fourth sector having a width in the range of approximately 1.5 to 2.5 milliseconds and a height in the range of approximately 25% to 35%;

a fifth sector having a width in the range of approximately 2.5 to 3.5 milliseconds and a height in the range of approximately 10% to 20%;

a sixth sector having a width in the range of approximately 2.5 to 3.5 milliseconds and a height in the range of approximately 5% to 15%; and a seventh sector having a width in the range of approximately 6.5 to 7.5 milliseconds and a height in the range of approximately 0% to 10%.

8. A method, as set forth in claim 7:

wherein the height of the first sector may not be less than the height of the second sector;

wherein the height of the fourth sector must be less than the height of the first sector; and wherein the height of the last four sectors must be less than the height of the first sector, and wherein the total width of the fourth through the seventh sectors must be less than the total width of the first, second and third sectors.

* * * * *